United States Patent [19]

Steffee

[11] Patent Number: 4,771,767
[45] Date of Patent: Sep. 20, 1988

[54] APPARATUS AND METHOD FOR MAINTAINING VERTEBRAE IN A DESIRED RELATIONSHIP

[75] Inventor: Arthur D. Steffee, Moreland Hills, Ohio

[73] Assignee: AcroMed Corporation, Cleveland, Ohio

[21] Appl. No.: 825,251

[22] Filed: Feb. 3, 1986

[51] Int. Cl.⁴ .............................................. A61F 5/04
[52] U.S. Cl. .................. 128/69; 128/92 YM
[58] Field of Search ............ 128/92 YM, 92 ZW, 69, 128/92 YF; 623/17

[56] References Cited

U.S. PATENT DOCUMENTS

| | | | |
|---|---|---|---|
| 3,242,922 | 3/1966 | Thomas | 128/92 YM |
| 3,426,364 | 2/1969 | Lumb | 623/17 |
| 4,401,112 | 8/1983 | Rezaian | 128/92 YM X |
| 4,553,273 | 11/1985 | Wu | 128/92 YM X |
| 4,611,580 | 9/1986 | Wu | 128/69 |
| 4,611,581 | 9/1986 | Steffee | 128/92 YF |

FOREIGN PATENT DOCUMENTS

| | | | |
|---|---|---|---|
| 2821678 | 11/1979 | Fed. Rep. of Germany | 128/69 |
| 3132520 | 6/1982 | Fed. Rep. of Germany | 128/92 YM |
| 839515 | 6/1981 | U.S.S.R. | 128/92 YM |

Primary Examiner—Clifford D. Crowder
Attorney, Agent, or Firm—Tarolli, Sundheim & Covell

[57] ABSTRACT

An apparatus and method for moving a vertebra to a desired relationship with other vertebrae and for maintaining the desired relationship. Mounting blocks are attached to the vertebrae. Pivot members are threaded onto a rod. The pivot members are received in the mounting blocks with the rod extending between two mounting blocks. The rod is rotated to move a vertebra relative to the other vertebrae. The mounting blocks are then tightened around the pivot members to maintain the vertebrae in the desired relationship.

5 Claims, 4 Drawing Sheets

APPARATUS AND METHOD FOR MAINTAINING VERTEBRAE IN A DESIRED RELATIONSHIP

BACKGROUND OF THE INVENTION

The present invention relates to the correction of spinal deformities. Specifically, it relates to moving a vertebra to a desired relationship with other vertebrae and maintaining the desired relationship.

Devices for correcting spinal column deformities are known. U.S. Pat. No. 3,997,138 discloses a device which has a pair of flexible rods or cables to maintain adjacent vertebrae in a desired relationship. The rods or cables are secured to fasteners connected with the vertebrae.

Devices which include rigid plates are also known for securing vertebrae in a desired relationship. The plates are relatively heavy. Each plate has longitudinal slots formed therein which do not permit flexibility in locating fasteners laterally in the vertebrae.

Another known device for correcting spinal deformities is a ratchet system. The ratchet system includes a rod and ratchet blocks which engage the rod. The rod spans several vertebrae. The ratchet blocks have hooks. The hooks grab around pedicles on the vertebrae. The hooks are then drawn together by the rod to apply a desired correction to the spinal column. The ratchet system can only compress the spinal column.

In another device, the corrective forces are applied by two steel rods which are wired around the spine. The rods are not directly attached to all the vertebrae that the rods span. Maintaining a desired spatial relationship among the vertebrae spanned by the rods is difficult.

Another known spinal corrective device is disclosed in U.S. Pat. No. 4,041,939. The device includes fasteners which are threaded into the vertebrae. A cable is threaded through openings in the head of each fastener. Tension is applied to the cable to move the vertebrae to a desired relationship. The fasteners are crimped around the cable to maintain the desired relationship. This device can only compress the spinal column. Once the cable is crimped into place, no further adjustment is possible.

SUMMARY OF THE INVENTION

The present invention provides a series of adjustable length links to move a vertebra to a desired relationship with other vertebrae and to maintain the vertebrae in the desired relationship. The links can be subjected to either compressive or tensile forces.

Each link interconnects two adjacent vertebrae. Each link is adjustable independent of the other links. Thus, the spacing between a pair of vertebrae can be adjusted while the spacing between other vertebrae is maintained constant.

Each link includes a rod having pivot members threaded on each end portion of the rod. The pivot members are connected with adjacent vertebrae by mounting blocks fastened to individual vertebra. To vary the spacing between the adjacent vertebrae, the rod is rotated in order to change the spacing between two pivot members. Thus, since the pivot members are connected with adjacent vertebrae, the space between the adjacent vertebrae is also varied.

BRIEF DESCRIPTION OF THE DRAWINGS

Further features of the present invention will become apparent to those skilled in the art to which the invention relates from a reading of the following specification made with reference to the accompanying drawings, in which.

DESCRIPTION OF SPECIFIC PREFERRED EMBODIMENTS

Figure 1:
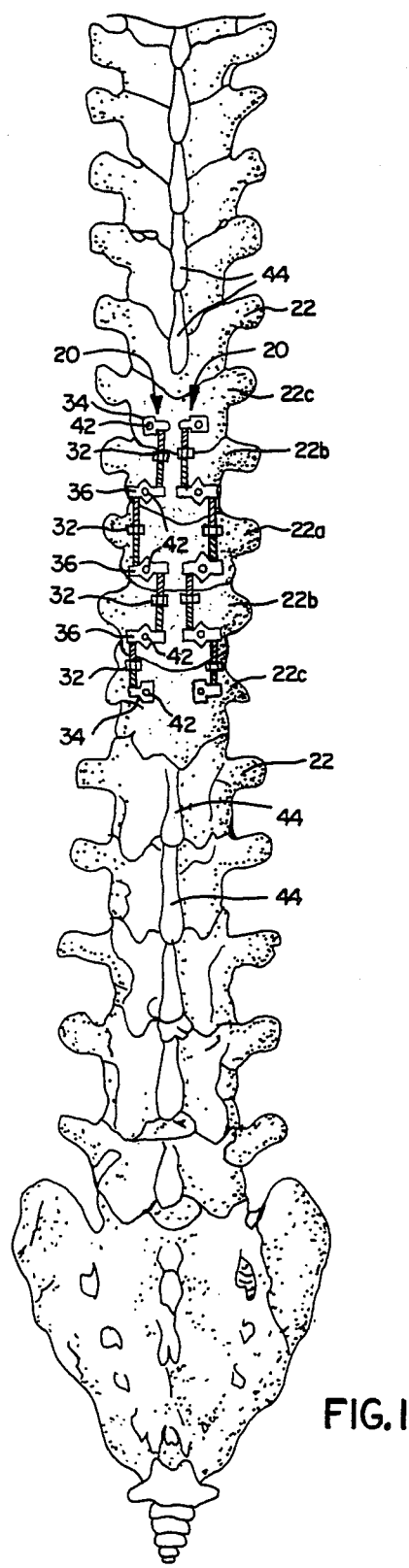
FIG. 1 is a dorsal view of a portion of a spinal column with an apparatus constructed in accordance with the present invention installed to maintain a desired relationship of the vertebrae.

A pair of assemblies 20 for moving a vertebra 22a to a desired relationship with other vertebrae 22b, 22c and for maintaining the desired relationship are illustrated in FIG. 1 connected with a human spinal column 24. Each of the assemblies 20 includes adjusting rods 32 connected with mounting blocks 34, 36 which are attached to individual vertebrae 22 by fastener assemblies 42.

The adjusting rods 32 are connected with the spinal column 24 to move a vertebra 22a to a desired relationship with other vetebrae 22b, 22c and to maintain the vertebrae 22 in a desired relationship. In order to maintain vertebra 22a in the desired relationship, as illustrated in FIG. 1, two adjacent vertebrae 22b, 22c on each side of vertebra 22a have the mounting blocks 34, 36 attached. This serves as an anchor from which to position vertebra 22a relative to. The vertebra 22a is moved relative to vetebrae 22b, 22c by rotating the adjusting rods 32 which interconnect the vertebra 22a with vertebrae 22b.

Before installing the assemblies 20, a vertebra 22a (FIG. 2) is displaced relative to adjacent vertebrae 22b, 22c which are in a desired relationship in the spinal column 24. The vertebra 22a is illustrated displaced in the dorsal and sagittal directions. It will be obvious that the vertebra 22a could be displaced in just the dorsal direction or just the sagital direction.

Figure 2:
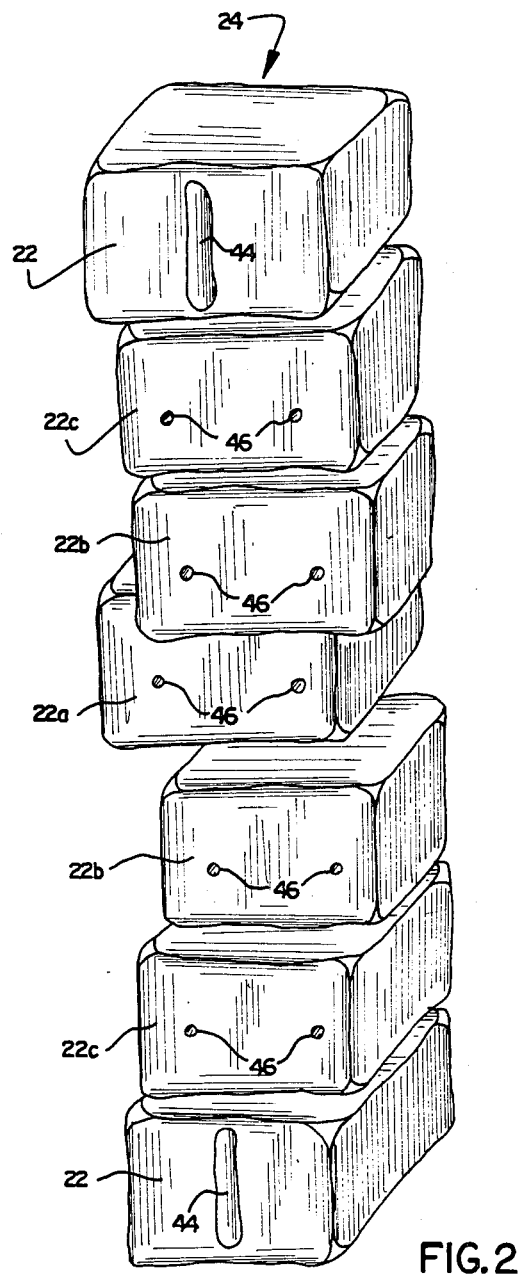
FIG. 2 is an enlarged schematic illustration of a spinal column having a displaced vertebra.

To install the assemblies 20, the spinous processes 44 (FIG. 2) must be removed from the vertebrae 22 which will have the assemblies 20 attached. The spinous processes 44 must be removed so that they will not interfere with the attachment and adjustment of the assemblies 20. FIG. 2 illustrates the spinous processes removed from the vertebrae 22a, 22b, and 22c which will have the assemblies attached.

Two openings 46 are formed in each of the vertebrae 22a, 22b, 22c for receiving force transmitting members. The openings are formed so that they will be in approximate vertical alignment when the vertebrae 22a, 22b, 22c are in the desired relationship. Force transmitting members 52 (FIG. 7) are then threaded into the openings 46 so that part of each force transmitting member extends from the vertebra 22.

Figure 6:
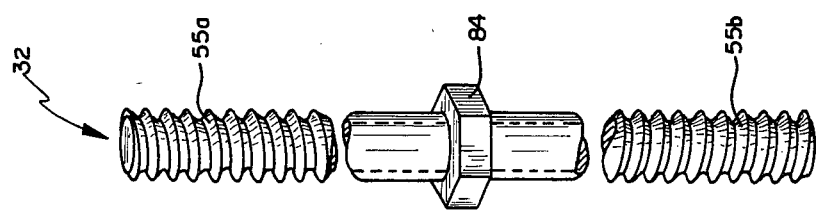
FIG. 6 is a perspective view illustrating an adjusting rod.

A first half 53a, 53b (FIGS. 7 and 8) of the mounting blocks 34, 36 for connecting pivot members 54 to the vertebrae 22 is received on the force transmitting member 52 which extends from the vertebra. Pivot members 54 are threaded onto the end portions of the adjusting rods 32. Each adjusting rod 32 (FIG. 6) has an end portion with a righthand thread 55a and an end portion with a lefthand thread 55b. The pivot members 54 (FIGS. 7 and 8) are received in chambers 58. A second half 62a, 62b of the mounting blocks 34, 36 is received on the force transmitting member 52. A nut 64 is sufficiently tightened onto the force transmitting member 52 to allow pivotal movement of the pivot members 54, but to restrict their rotational movement, relative the mounting blocks 34, 36. Each adjusting rod 32 is rotated to move the vertebrae 22 to a desired relationship. The direction of rotation of the adjusting rod 32 depends upon whether the distance between the pivot members 54 threaded onto the rod is to increase or decrease. The nut 64 is then further tightened to prevent any pivotal movement of the pivot joint 54 to maintain the vertebrae 22 in the desired relationship.

Figure 4:
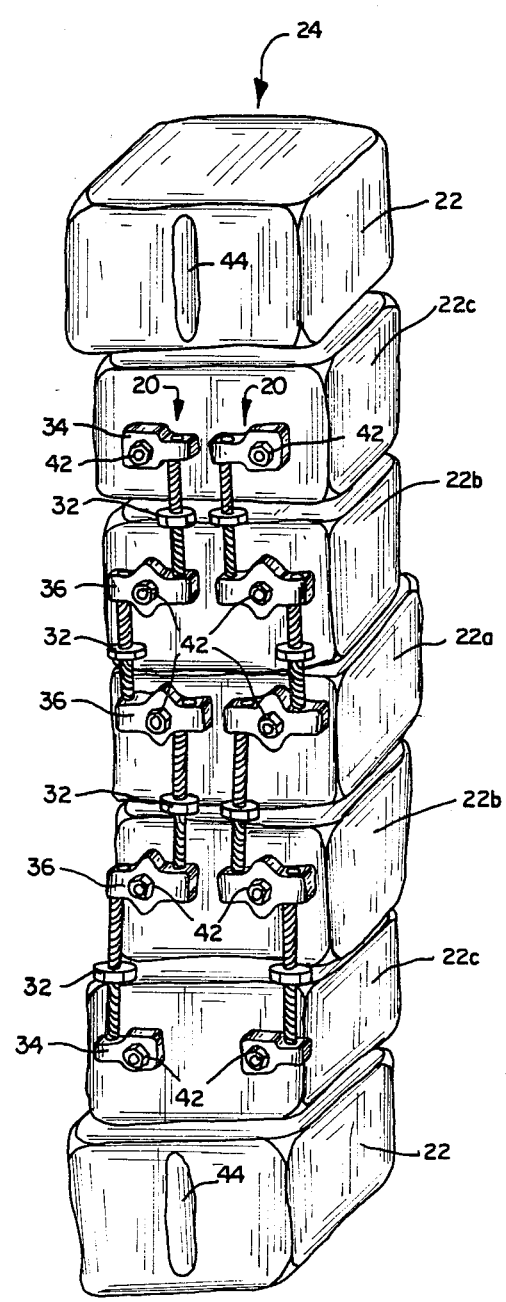
FIG. 4 is an enlarged schematic view, similar to FIG. 3, illustrating the present invention installed on a spinal column after moving the displaced vertebra to the desired relationship.
Figure 5:
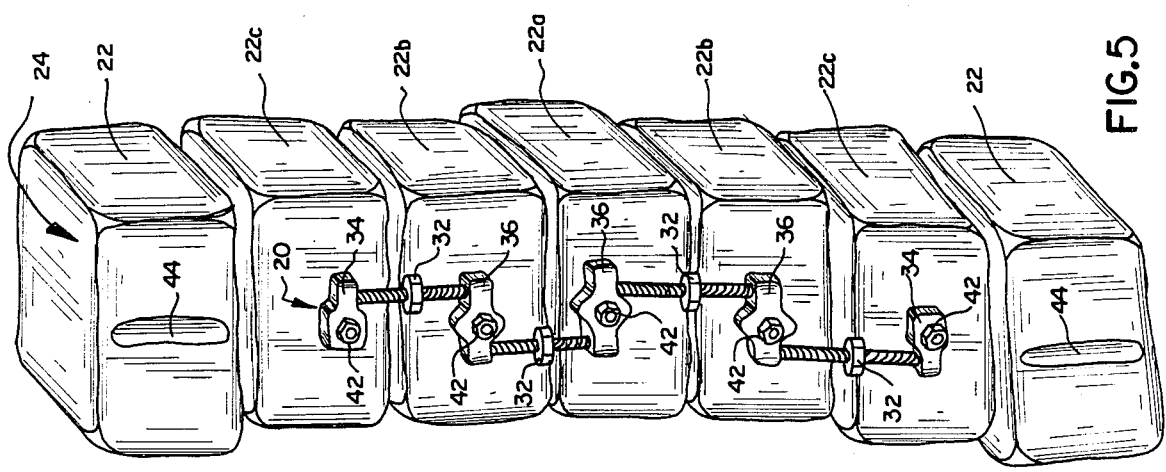
FIG. 5 is an enlarged schematic view, similar to FIG. 4, illustrating another application of the present invention installed on a spinal column.

An alternative application of the present invention is illustrated in FIG. 5. A single assembly 20 is attached to the spinal column 24 to maintain the vertebrae 22 in a desired relationship. The structure of the single assembly 20 in FIG. 5 is the same as that for either of the assemblies in FIG. 4.

Figure 7:
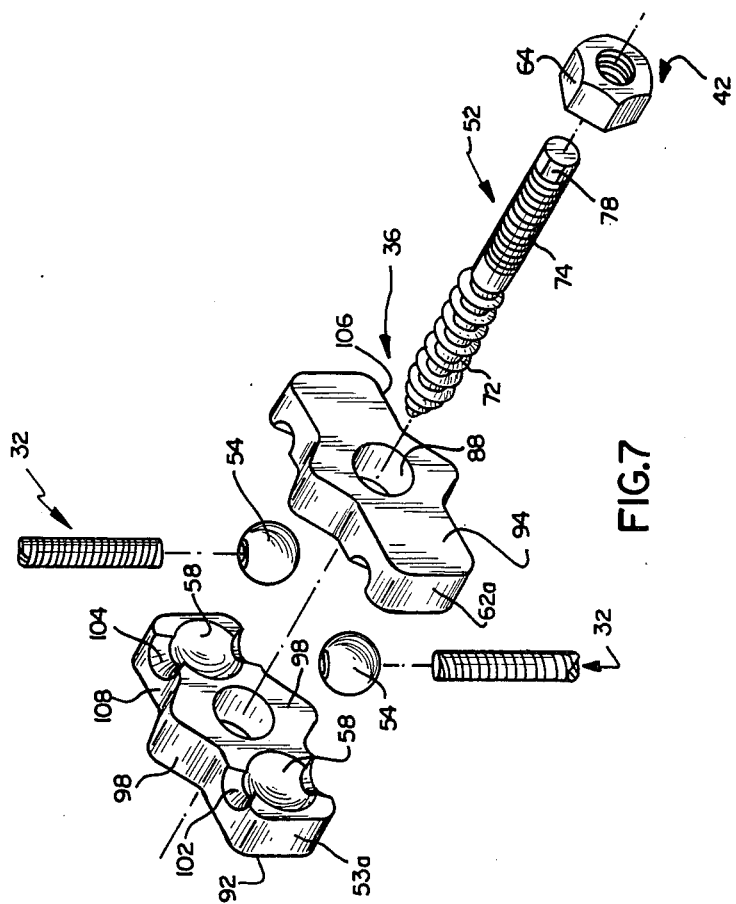
FIG. 7 is an exploded fragmentary perspective view illustrating dual spherical pivot members, a mounting block, adjusting rods, and fastener assembly of the apparatus in FIG. 1.
Figure 8:
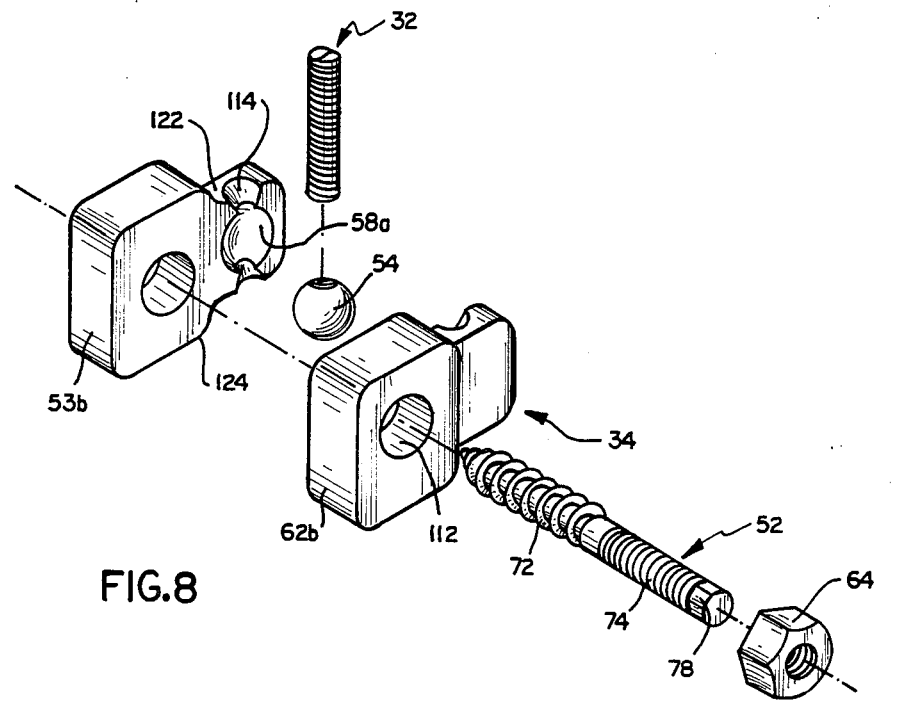
FIG. 8 is an exploded fragmentary perspective view illustrating a single spherical pivot member, mounting block, adjusting rod, and fastener assembly of the apparatus in FIG. 1.

The fastener assembly 42 (FIG. 4) connects a mounting block 34 or 36 with a vertebra 22 and presses the mounting block against the pivot members 54 (FIGS. 7 and 8). The fastener assembly 42 includes a force transmitting member 52 having a first threaded portion 72 and a second threaded portion 74. The first threaded portion 72 has a relatively large diameter helix for threading into an opening 46 formed in a vertebra 22. The first threaded portion 72 has a substantially larger crest diameter than the inside diameter of the opening 46.

As the first threaded portion 72 is threaded into the opening 46, the helix cuts into the cylindrical side surface of the opening to firmly attach the force transmitting member 52 to the vertebra 22. The force transmitting member 52 is threaded into the vertebra 22 by placing a tool (not shown) on the hex head portion 78. The tool and force transmitting member 52 are then rotated until the desired depth of engagement with the vertebra 22 is obtained. The force transmitting member 52 is made from a surgical grade stainless steel or titanium.

The second threaded portion 74 of the force transmitting member 52 has a standard external screw thread for engaging standard internal threads of the nut 64. The nut 64 has a standard hexagonal external configuration for a suitable tool to engage for rotating the nut relative to the second threaded portion 74. The nut 64 is rotated until it abuttingly engages a side of the second half 62a, 62b of a mounting block 34, 36. Initially, the nut 64 is rotated until the mounting block 34, 36 is pressed against the vertebra 22 with sufficient force to prevent the pivot member 54 from rotating but allowing pivotal movement. The adjusting rods 32 are then rotated about their longitudinal axes to position the vertebrae 22 in a desired relationship. The nut 64 is then rotated to a final position where the pivot member 54 is prevented from further pivotal movement, in order to maintain the vertebrae 22 in the desired relationship. The threaded portion 74 which extends beyond the nut 64 is then trimmed off adjacent to the nut. Force transmitting member 52 has the same general construction disclosed in U.S. Pat. No. 4,611,581 for "Apparatus for Straightening Spinal Cclumns", by Arthur D. Steffee.

Figure 3:
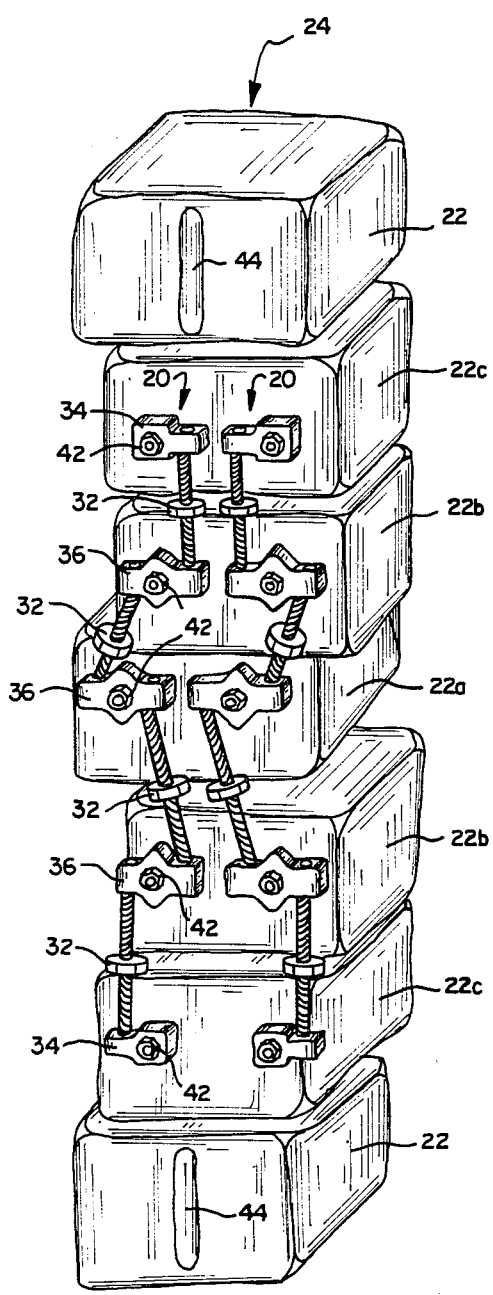
FIG. 3 is an enlarged schematic view, similar to FIG. 2, illustrating the apparatus installed on a spinal column before moving the displaced vertebra to a desired relationship.

The adjusting rod 32 (FIGS. 3 and 4) interconnects, varies, and maintains the position of two vertebrae 22. The adjusting rod 32 is made from a surgical grade stainless steel or titanium. Before each adjusting rod 32 (FIG. 6) is installed to connect two vertebrae 22, it has a pair of pivot members 54 (FIG. 7) threaded onto end portions. One end portion 55a has righthand threads and the other end portion 55b has lefthand threads. This forces the pivot members 54 to move in opposite directions along the rod 32 upon rotation of the rod about its longitudinal axis to effect relative movement between two vertebrae 22. The pivot members 54 are threaded so that the axis of the threaded portion passes approximately through the center of the pivot member.

The adjusting rod 32 having pivot members 54 threaded onto end portions essentially creates a rigid link of adjustable length which can pivot at its two end portions. The link could have just one pivot member 54 threaded onto one end portion, while the other end portion has a pivot member rigidly connected or integrally formed thereon.

After the pivot members 54 are clamped by the mounting block 34, 36 and prevented from relative rotation, the adjusting rod 32 is rotated to change the distance between two vertebrae 22. When the rod is rotated in a first direction, because of the righthand and lefthand threaded end portions, the distance between the pivot members 54 will increase. If the adjusting rod 32 is rotated in a second direction, the distance between the pivot members 54 will decrease. The interaction of the adjusting rod 32 and pivot members 54 is similar to that of a turnbuckle. Thus, since the pivot members 54 are connected with the vertebrae 22 by the mounting blocks 34, 36, rotation of the adjusting rod 32 effects a change in the relative position of the two vertebrae.

The adjusting rod 32 is rotated by gripping the hex head portion 84 (FIG. 6) with a suitable tool (not shown) and rotating the tool. The hex head portion 84 is integrally formed on the adjusting rod 32. Alternative means for rotating the adjusting rod 32 can be provided. For example, the adjusting rod 32 could have an intermediate portion of the shaft itself formed with a hexagonal or square configuration and be about the same diameter as the threaded end portions 55a, 55b.

The mounting blocks 34, 36 (FIGS. 7 and 8) connect the pivot members 54 with the vertebrae 22 and prevent movement of the pivot members relative to the vertebrae. The mounting blocks 34, 36 are designed to accept a pair of pivot members 54, as illustrated in FIG. 7, or a single pivot member, as illustrated in FIG. 8. The mounting blocks 34, 36 are made from a material which is compatible with human tissue, generally a surgical grade stainless steel or titanium.

FIG. 7 illustrates the mounting block 36 used on intermediate vertebrae 22a, 22b (FIG. 4) for connecting a pair of spherical pivot members 54 with the vertebrae. The mounting block 36 has a first half 53a and a second half 62a. Each half 53a, 62a has a pair of surfaces which define generally spherical chambers 58 for receiving the pivot members 54. The size of the spherical chamber 58 is such that it will prevent the pivot member 54 from pivotal movement relative to the mounting block 36 when the nut 64 is tightened against the mounting block. That is, the diameter of the spherical chamber 58 is equal to or slightly smaller than the diameter of the spherical pivot member 54. This permits the spherical chamber 58 to grip the member 54 for preventing pivotal movement when the nut is tightened to its final position against the mounting block.

The mounting block 36 has a first opening 88 through first side 92 and second side 94 of the mounting block 36 for receiving the force transmitting member 52 therethrough. The first side 92 engages a vertebra 22. The second side 94 engages the nut 64 for pressing the mounting block 36 to the vertebra 22 and around the pivot members 54. A pair of protrusions 98 extend from the mounting block 36 around the opening 88 to add strength to the mounting block 36 and surface area for the vertebra 22 and nut 64 to engage. The size and configuration of the protrusions 98 depends upon the overall dimensions of the mounting block 36 and opening 88. It will be obvious, for example, that the protrusions 98 can have a squared or rounded configuration.

The mounting block 36 has second and third openings 102, 104 respectively, which extend through third and fourth sides 106, 108 respectively, of the mounting block. The openings 102, 104 are transverse to the first opening 88. The openings 102, 104 have their longitudinal axes pass approximately through the center of spherical chambers 58 to allow the adjusting rods 32 to pass through for connection with the pivot members 54 and to pivot. The openings 102, 104 are illustrated as countersunk but can be of a cylindrical configuration. The diameter of the openings 102, 104 is smaller than that of the spherical chamber 58 and larger than the diameter of the adjusting rod 32. It will be obvious that it is not necessary for the openings 102, 104 to extend completely through the mounting block 36. For example, opening 102 could extend just through side 106, while opening 104 could extend just through side 108.

FIG. 8 illustrates a mounting block 34 used on the extreme ends of the assembly 20 (FIGS. 1, 4 and 5) for connecting a single spherical pivot member 54 with a vertebra 22. The design and function of the mounting block 34 (FIG. 8) is similar to that described above for mounting block 36. That is, the mounting block 34 has a first half 53b and a second half 62b. A first opening 112 for receiving the force transmitting member 52 extends through both halves 53b, 62b. The mounting block 34 has a single spherical chamber 58a for receiving the spherical pivot member 54. A second opening 114 extends through the top 122 and bottom 124 of the mounting block 34 for allowing the adjusting rod 32 to pass through and pivot relative to the mounting block. The second opening 114 is transverse to the first opening 112.

Figure 9:
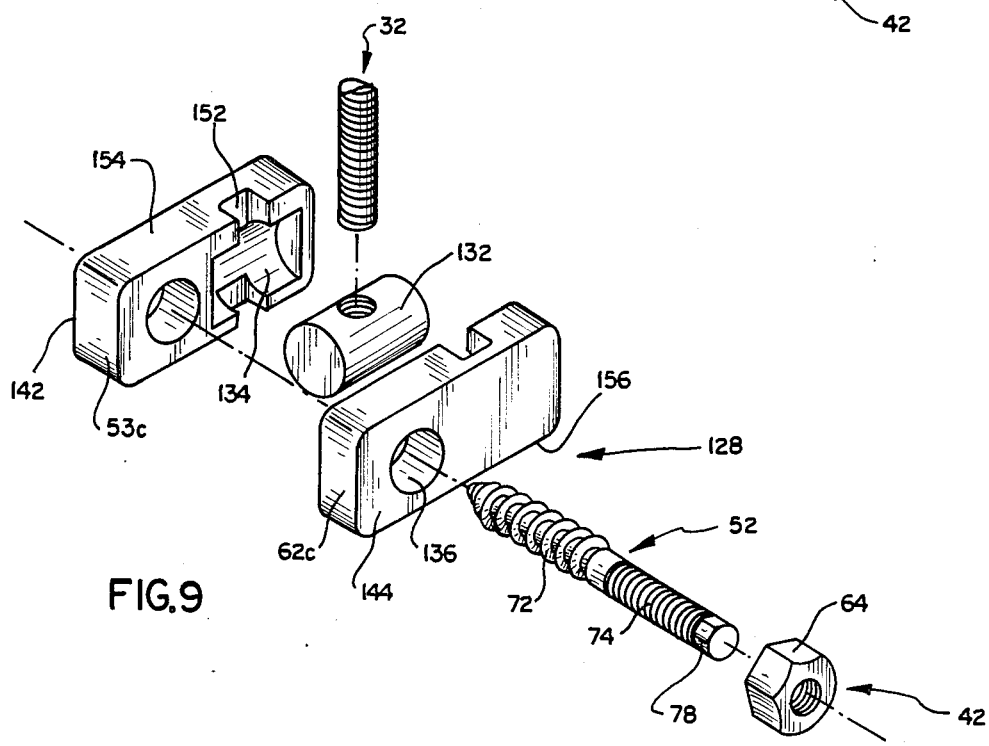
FIG. 9 is a partially exploded fragmentary perspective view illustrating a single cylindrical pivot member, adjusting rod, and fastener assembly.

FIG. 9 illustrates a cylindrical pivot joint 132 which allows pivotal movement only in the dorsal plane when the mounting block 128 is connected with a vertebra 22. The mounting block 128 has a first half 53c and a second half 62c. The mounting block 128 has a cylindrical chamber 134 for receiving the cylindrical pivot member 132. The mounting block 128 has a first opening 136 extending through a first side 142 and a second side 144 of the mounting block 128.

The cylindrical configuration of the pivot member 132 prevents the pivot member from rotating relative to the mounting block when the adjusting rod 32 is rotated. Therefore, the force exerted by the nut 64 on the second side 144 of the mounting block 128 is not as critical as it would be for the spherical pivot member 54 arrangement to prevent rotation of the pivot member 54.

A second opening 152 is transverse to the first opening 136 and extends through a third side 154 and a fourth side 156 for allowing the adjusting rod 32 to engage the pivot member 132. The second opening 152 is illustrated as being rectangular. It will be obvious that the second opening 152 can also be cylindrical as described above for mounting blocks 34 and 36 or tapered outwardly. It will also be obvious that a mounting block can be designed that will accept a pair of cylindrical pivot members 132 so that it can be used as an intermediate connector in the assembly 20 illustrated in FIG. 1.

In summary, an improved apparatus and method is provided for moving a vertebra 22a relative to other vertebrae 22b, 22c to a desired relationship and for maintaining the desired relationship. Mounting blocks 34, 36 are attached to individual vertebrae 22 and interconnected by a plurality of adjusting rods 32. Pivot members 54 are threaded onto threaded portions 55a, 55b of the adjusting rods 32 and received in the mounting blocks 34, 36. The relationship among vertebrae 22 is changed when the adjusting rods 32 are rotated thereby moving one vertebra relative to the other vertebrae.

Having described my invention, I claim:

1. A method for moving a first vertebra to a desired relationship with a second vertebra and for maintaining the first and second vertebrae in a desired relationship, said method comprising:

forming an opening in a first vertebra;

forming an opening in a second vertebra;

threading fasteners into the openings in the first and second vertebrae;

providing mounting blocks for attachment with the first and second vertebrae, each of the mounting blocks having first and second halves which cooperate to form a chamber for receiving a pivot member;

placing a first half of one mounting block onto the fastener in the first vertebra and a first half of another mounting block onto the fastener in the second vertebra;

providing a first pivot member having a righthand internally threaded portion and a second pivot member having a lefthand internally threaded portion;

providing a rod having a first end portion with a righthand thread and a second end portion with a lefthand thread;

threading the first pivot member onto the first end portion of the rod;

threading the second pivot member onto the second end portion of the rod;

placing the first pivot member into the portion of the chamber formed in the first half of the one mounting block on the first vertebra with the rod extending from the one mounting block towards the second vertebra;

placing the second pivot member into the chamber in the other mounting block on the second vertebra;

placing a second half of the one mounting block onto the fastener in the first vertebra;

placing a second half of the other mounting block onto the fastener in the second vertebra;

tightening nuts on respective fasteners with sufficient force to clamp the mounting blocks around the respective pivot members allowing pivotal movement of the pivot members relative to the mounting blocks and preventing rotational movement of the pivot members about the longitudinal central axis of the rod;

rotating the rod relative to the first and second pivot members to move the first vertebra relative to the second vertebra to a desired relationship; and thereafter, tightening the nuts against the mounting blocks preventing pivotal and rotational movement of the pivot members relative to the mounting blocks thereby maintaining the desired relationship.

2. An apparatus comprising:
a first mounting block connectible with a first vertebra;
a second mounting block connectible with a second vertebra;
first fastening means for extending through an opening in said first mounting block to connect said first mounting block with a first vertebra;
second fastening means for extending through an opening in said second mounting block to connect said second mounting block with the second vertebra;
rod means rotatable about its longitudinal central axis extending between said first and second mounting blocks; and
means for pivotally connecting a first end portion of said rod means with said first mounting block and a second end portion of said rod means with said second mounting block and for supporting said rod means for rotation relative to said first and second mounting blocks, said means for pivotally connecting having a threaded portion cooperating with a threaded end portion of said rod means to effect relative movement of the first and second vertebrae upon rotation of said rod means;
each of said first and second mounting blocks including a pair of halves, each of said pair of halves having a surface defining a portion of a chamber for receiving said means for pivotally connected when said halves are pressed together by tightening said respective fastening means against said mounting block, said mounting block also having a surface defining another opening for receiving said rod means therein and extending through said mounting block to said chamber in a direction transversely to said opening for said fastening means.

3. An apparatus as set forth in claim 2 wherein said means for pivotally connecting includes pivot members of a generally spherical configuration, each of said pivot members having an internally threaded portion passing approximately through the center of said pivot member for receiving said externally threaded end portion of said rod means, said chamber in each of said first and second mounting blocks being of a generally spherical configuration for receiving a respective one of said pivot members.

4. An apparatus as set forth in claim 2 wherein said means for pivotally connecting includes pivot members of a generally cylindrical configuration, each of said pivot members having an internally threaded portion transversely intersecting the longitudinal axis of said pivot member for receiving said externally threaded end portion of said rod means, said chamber in each of said first and second mounting blocks being of a generally cylindrical configuration for receiving a respective one of said pivot members.

5. An apparatus comprising:
a first mounting block connectible with a first vertebra;
a second mounting block connectible with a second vertebra;
first fastening means for connecting said first mounting block with the first vertebra;
second fastening means for connecting said second mounting block with the second vertebra;
rod means rotatable about its longitudinal central axis extending between said first and second mounting blocks; and
means for pivotally connecting a first end portion of said rod means with said first mounting block and for pivotally connecting a second end portion of said rod means with said second mounting block and for supporting said rod means for rotation relative to said first and second mounting blocks, said means for pivotally connecting having a threaded portion cooperating with a threaded end portion of said rod means to effect relative movement of the first and second vertebrae upon rotation of said rod means;
each of said first and second mounting blocks including a pair of halves, each of said pair of halves having a surface defining a portion of a chamber for receiving said means for pivotally connecting when said halves are pressed together, each of said pair of halves also having a surface defining a first opening in each of said first and second mounting blocks and which first opening extends through said mounting block to said chamber for receiving said rod means, each of said first and second mounting blocks including a surface defining a second opening therethrough and extending in a direction transverse to said first opening, said first and second fastening means extending through the respective second opening in each respective mounting block to press said halves of said mounting blocks together.

* * * * *